United States Patent
Wang

(10) Patent No.: US 10,495,559 B2
(45) Date of Patent: Dec. 3, 2019

(54) PARTICLE CONCENTRATION SENSING METHOD AND PORTABLE ELECTRONIC APPARATUS APPLYING THE PARTICLE CONCENTRATION SENSING METHOD

(71) Applicant: PixArt Imaging Inc., Hsin-Chu (TW)

(72) Inventor: Guo-Zhen Wang, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 0 days.

(21) Appl. No.: 15/822,225

(22) Filed: Nov. 27, 2017

(65) Prior Publication Data

US 2019/0162642 A1    May 30, 2019

(51) Int. Cl.
| | |
|---|---|
| *G01N 15/06* | (2006.01) |
| *G01N 21/53* | (2006.01) |
| *G01J 1/02* | (2006.01) |
| *G01N 15/00* | (2006.01) |

(52) U.S. Cl.
CPC ............. *G01N 15/06* (2013.01); *G01N 21/53* (2013.01); *G01J 1/0295* (2013.01); *G01N 2015/03* (2013.01)

(58) Field of Classification Search
CPC .............. G01N 15/06; G01N 15/0205; G01N 15/1463; G01N 15/1459; G01N 21/53; G01N 2015/03; G01N 2015/025; G01N 2015/1493; G01N 2015/1486; G01J 1/0295; F24F 11/0079; F24F 11/006; F24F 11/0034; F24F 11/015
See application file for complete search history.

(56) References Cited

U.S. PATENT DOCUMENTS

| | | | |
|---|---|---|---|
| 2008/0146892 A1* | 6/2008 | LeBoeuf | G16H 50/30 600/300 |
| 2014/0266682 A1* | 9/2014 | Gettings | G08B 23/00 340/517 |
| 2014/0300888 A1* | 10/2014 | Duffey | G01S 17/58 356/28 |
| 2015/0077737 A1* | 3/2015 | Belinsky | G01N 15/0211 356/51 |
| 2016/0058375 A1* | 3/2016 | Rothkopf | G06F 1/1643 600/301 |
| 2016/0239802 A1* | 8/2016 | Burch, V | H04W 4/70 |
| 2017/0322133 A1* | 11/2017 | Trainer | G01J 3/0218 |
| 2017/0328982 A1* | 11/2017 | Jongsma | B63C 7/26 |
| 2017/0350610 A1* | 12/2017 | Michielsen | F24F 11/0001 |

* cited by examiner

*Primary Examiner* — Sang H Nguyen
(74) *Attorney, Agent, or Firm* — Winston Hsu

(57) ABSTRACT

A portable electronic apparatus can sense particle concentration, comprising: a motion detector, configured to detect a motion of the portable electronic apparatus; a first light source, configured to emit first light, wherein first scattered light is generated while the first light emitting particles in air; a light sensor, configured to sense the first scattered light; and a processor, configured to calculate a first particle concentration based on the motion and the first scattered light sensed by the light sensor. Via such apparatus, the particle concentration can be calculated without a fan, and the accuracy for calculating particle concentration can be increased if more than one light source is employed.

18 Claims, 10 Drawing Sheets

| Moving speed (cm/sec) | Fan speed (RPM) |
|---|---|
| MS_1 | FS_1 |
| MS_2 | FS_2 |
| MS_3 | FS_3 |

PARTICLE CONCENTRATION SENSING METHOD AND PORTABLE ELECTRONIC APPARATUS APPLYING THE PARTICLE CONCENTRATION SENSING METHOD

BACKGROUND OF THE INVENTION

1. Field of the Invention

The present invention is related with a particle concentration sensing method and a portable electronic apparatus applying the method, and particularly relates to a particle concentration sensing method which does need a fan and a portable electronic apparatus applying the method.

2. Description of the Prior Art

Conventionally, a particle concentration sensing apparatus, which can sense particulate matter (ex. PM 2.5) in the air, always needs a fan. Via operation of the fan, air can flow into the particle concentration sensing apparatus and flows out the particle concentration sensing apparatus. However, the fan increases either the size or the cost of the particle concentration sensing apparatus.

Besides, the sensed particle concentration is always non-accurate since the conventional particle concentration sensing apparatus uses only a single light source to sense particulate matter.

Additionally, the conventional particle concentration sensing apparatus always applies a photodiode array to sense light. The photodiode array has a large size, thus accordingly increases the size of the particle concentration sensing apparatus.

SUMMARY OF THE INVENTION

One objective of the present invention is to provide a portable electronic apparatus can sense particle concentration without a fan.

Another embodiment of the present invention is to provide a particle concentration sensing method can sense particle concentration without a fan.

One embodiment of the present invention is to provide a portable electronic apparatus can sense particle concentration, comprising: a motion detector, configured to detect a motion of the portable electronic apparatus; a first light source, configured to emit first light, wherein first scattered light is generated while the first light emitting particles in air; a light sensor, configured to sense the first scattered light; and a processor, configured to calculate a first particle concentration based on the motion and the first scattered light sensed by the light sensor.

Another embodiment of the present invention is to provide a particle concentration sensing method, applied to a portable electronic apparatus, comprising: (a) generating first light; (b) sensing first scattered light, wherein the first scattered light is generated while the first light emitting particles in air; and (c) calculating a first particle concentration based on the motion and the first scattered light sensed by the light sensor.

One embodiment of the present invention discloses: A portable electronic apparatus can sense particle concentration, comprising: a light sensor, configured to sense first scattered light passing through particles in air and output a sensed optical data corresponding to the first scattered light; and a processor, configured to receive the sensed optical data and a motion data representing a motion of the portable electronic apparatus to calculate a first particle concentration.

In view of above-mentioned embodiments, the particle concentration can be calculated without a fan, and the accuracy for calculating particle concentration can be increased since more than one light source is employed. Further, applying a CMOS light sensor can decrease the size of the light sensor.

These and other objectives of the present invention will no doubt become obvious to those of ordinary skill in the art after reading the following detailed description of the preferred embodiment that is illustrated in the various figures and drawings.

DETAILED DESCRIPTION

Following embodiment(s) of the present invention can be realized by a computer of a system or apparatus that reads out and executes computer executable instructions (e.g., one or more programs) recorded on a storage medium (which may also be referred to more fully as a non-transitory computer-readable storage medium') to perform the functions of one or more of the following embodiment(s) and/or that includes one or more circuits (e.g., application specific integrated circuit (ASIC)) for performing the functions of one or more of the following embodiment(s). The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Figure 1A:
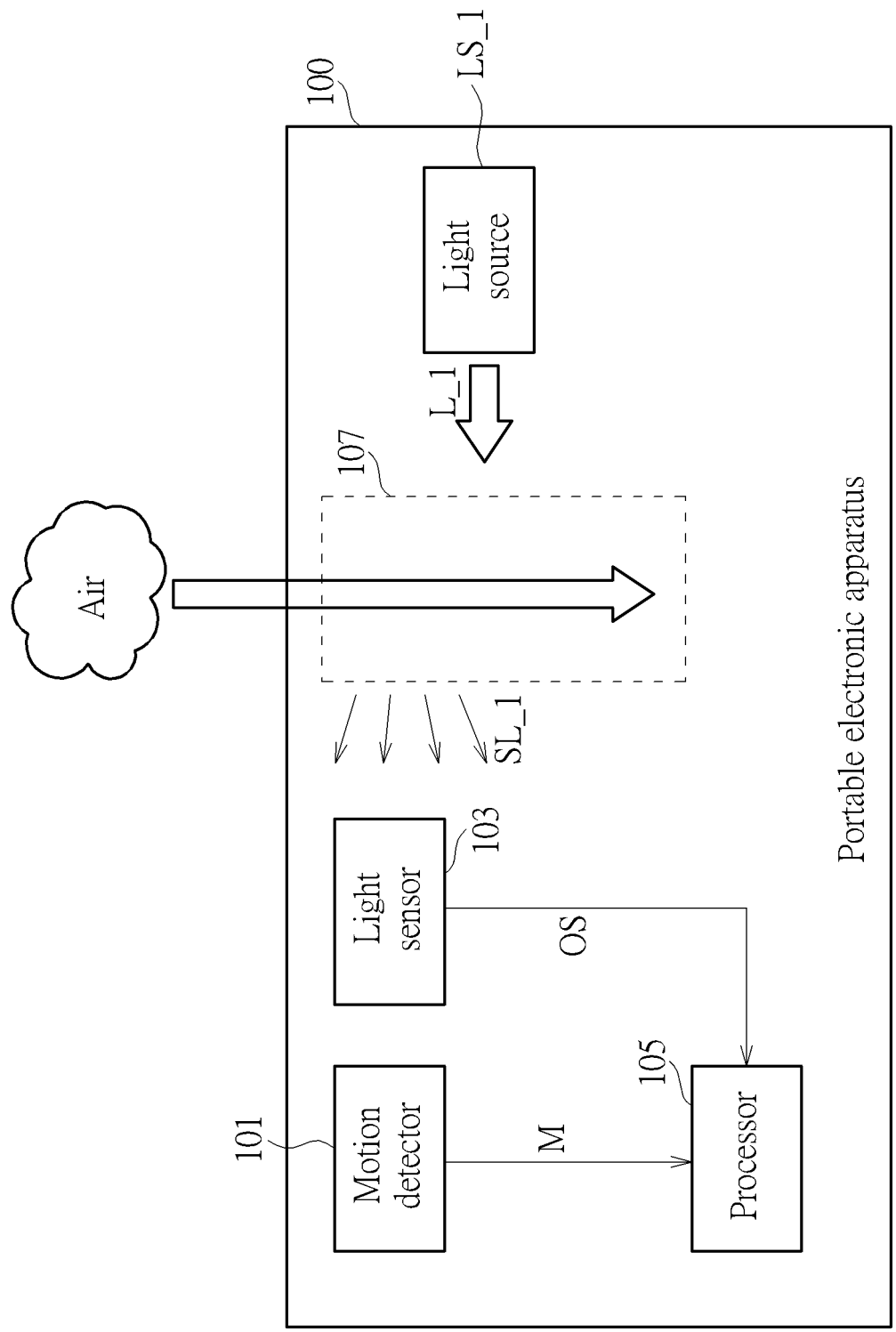
FIG. 1A and FIG. 1B are block diagrams illustrating portable electronic apparatus according to different embodiments of the present invention.
Figure 1B:
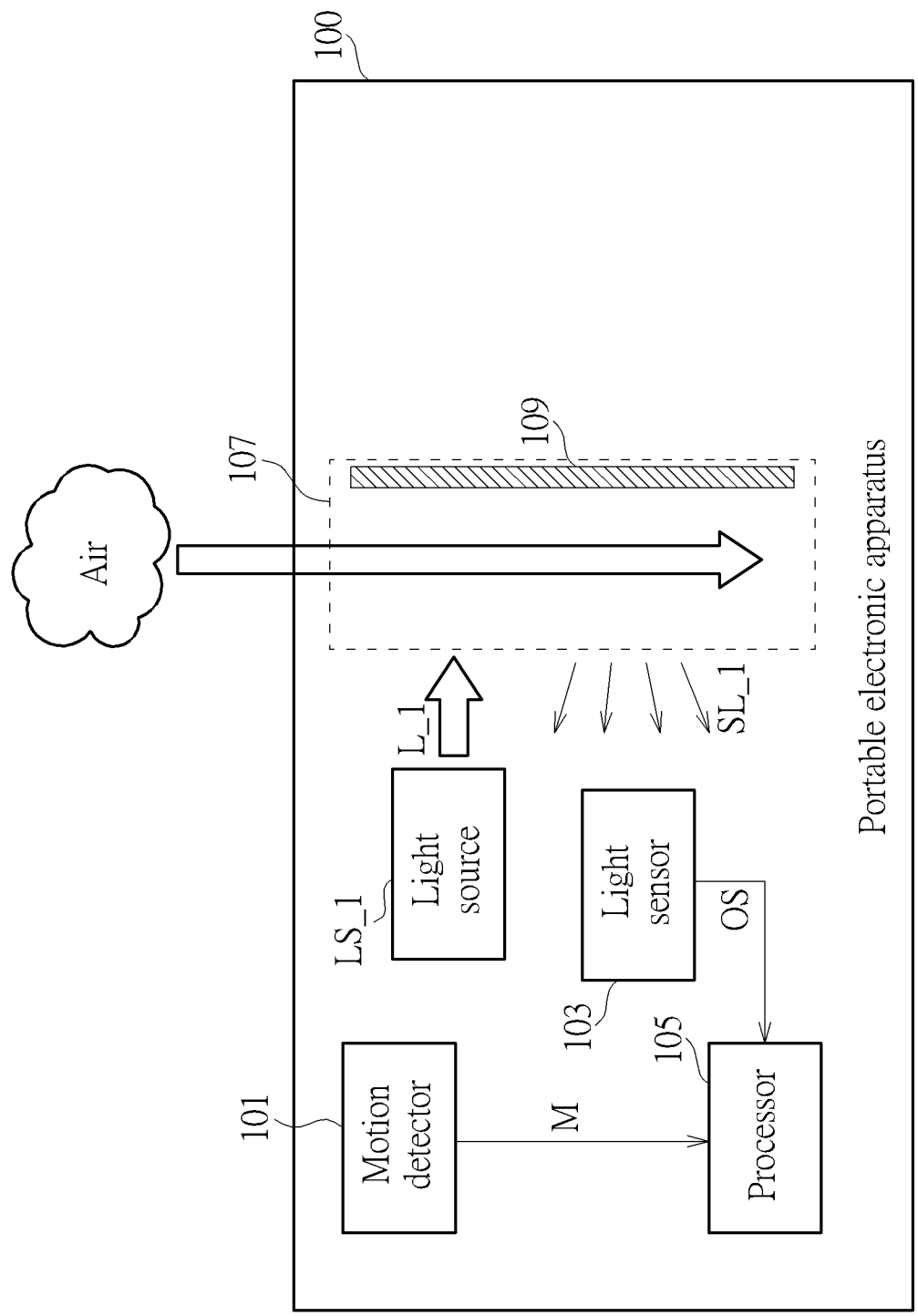

FIG. 1A and FIG. 1B are block diagrams illustrating portable electronic apparatus according to different embodiments of the present invention. As illustrated in FIG. 1A, the portable electronic apparatus 100 comprises a motion detector 101, a light source LS_1, a light sensor 103 and a processor 105.

The processor 105 is used to control the operation of the motion detector 101, the light source LS_1 and the light sensor 103 to perform a particle sensing operation. Further, in one embodiment, the processor 105 is employed to control other operations for the portable electronic apparatus 100 besides the particle sensing operation. For example, the portable electronic apparatus 100 is a wearable electronic apparatus such as a smart watch. In such embodiment, besides the particle sensing operation, the processor 105 can further control other operations for the portable electronic apparatus, such as display time or play music.

The light source LS_1 can be any component that can emit light, for example, a LED (light emitting diode).

The motion detector 101 is configured to detect a motion of the portable electronic apparatus 100, such as a moving speed or a moving acceleration and generating a motion data M representing the motion of the portable electronic apparatus 100. In one embodiment, the motion detector 101 is an accelerometer or a gyroscope.

The light sensor 103 is configured to sense a scattered light SL_1 and to generate an optical sensed data OS corresponding to the scattered light SL_1, wherein the scattered light SL_1 is generated from light passing through or reflected from particles. In one embodiment the optical sensed data OS includes an image of the scattered light SL_1 or a digital statistic data generated from the scattered light SL_1. The way to calculate optical sensed data OS from the scattered light SL_1 to determine a particle concentration is well known and will not be described detail thereinafter.

The processor 105 is configured to calculate a particle concentration for the air flowing into the portable electronic apparatus 100 based on the motion data M and the optical sensed data OS. Since the concentration for particle in the air affects the generation of the scattered light SL_1, the processor 105 can calculate the particle concentration based on the optical sensed data OS, such as the distribution of the scattered light SL_1 (ex. a light amount, an emitting direction or a light intensity of the scattered light SL_1). For example, if more particle matters are contained in the air, more scattered light SL_1 is generated. On the contrary, if no particle matter is contained in the air, no scattered light SL_1 is generated, or only few scattered light SL_1 is generated, and the image of the scattered light SL_1 will be flat in its intensity distribution. In one embodiment, the light sensor 103 is a CMOS (Complementary Metal-Oxide-Semiconductor) light sensor.

The light source LS_1 is configured to emit light L_1, so that the scattered light SL_1 could be generated while the light L_1 emits particles in the air. In the embodiment illustrated in FIG. 1A, the portable electronic apparatus 100 comprises a cavity 107. The air outside the portable electronic apparatus 100 will flow into the cavity 107 if the portable electronic apparatus 100 moves.

In the embodiment of FIG. 1A, since the motion of the portable electronic apparatus 100 affects the speed or the amount for the air flowing into the portable electronic apparatus 100, the processor 105 further refers to the motion data M to calculate the particle concentration. In one embodiment, the processor 105 maps the motion data M to a fan speed, and then calculates the particle concentration based on the fan speed and the scattered light SL_1 sensed by the light sensor 103.

The components in FIG. 1A can be integrated to a single device such as a module, a chip or a circuit. In one embodiment, the light sensor 103 and the processor 105 are integrated to a single device. By this way, the light sensor 103 and the processor 105 can be easily assembled to the portable electronic apparatus 100.

Besides, in the embodiment of FIG. 1A, the light source LS_1 and the light sensor 103 are provided at different sides of the cavity 107. However, the light source LS_1 and the light sensor 103 can be provided at the same side. As illustrated in FIG. 1B, a reflector 109 is provided in the cavity 107. In such embodiment, the light source LS_1 emits light L_1 to the air in the cavity 107, and at least part of the light L_1 is reflected by the reflector 109. Also, the reflector 109 may reflects some scattered light generated by the light L_1. After that, the light sensor 103 receives the scattered light SL_1 generated by the reflected light from the reflector 109.

Figures 2, 3:
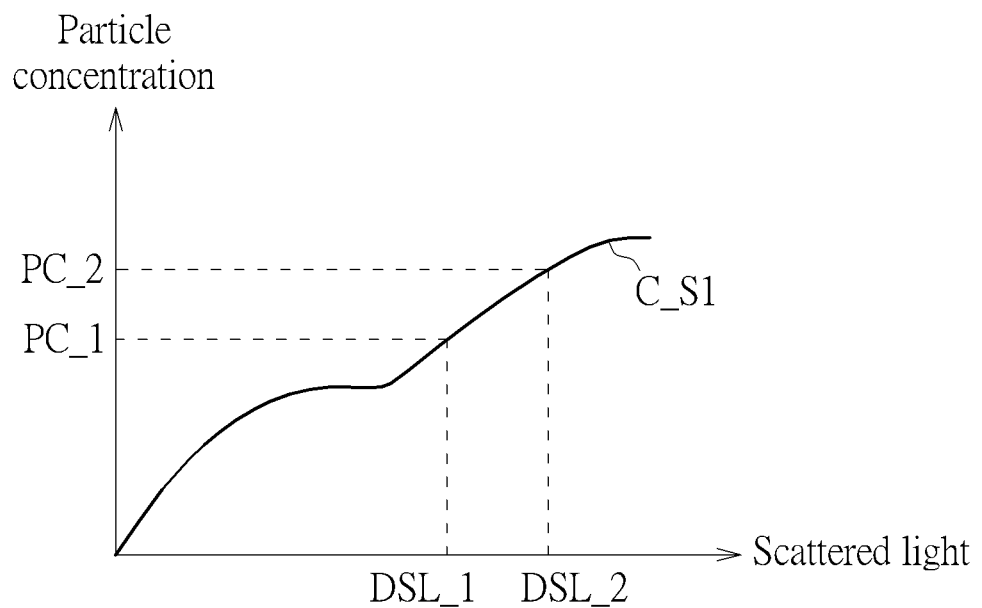
FIG. 2 is a schematic diagram illustrating an example for a mapping table for mapping a moving speed to a fan speed.
FIG. 3 is a schematic diagram illustrating an example for a relation curve indicating relations between the particle concentration and the scattered light, for the embodiment illustrated in FIG. 1A.

FIG. 2 is a schematic diagram illustrating an example for a mapping table for mapping a moving speed to a fan speed. As illustrated in FIG. 2, the moving speed (i.e. the above-mentioned motion) of the portable electronic apparatus 100 can be mapped to the fan speed based on the mapping table 200. Such mapping table can be recorded in a storage device (ex. a memory) in the portable electronic apparatus 100. However, the mapping table 200 is not limited to be recorded in the storage device in the portable electronic apparatus 100. For example, the portable electronic apparatus 100 can read the mapping table from a network while needed.

FIG. 3 is a schematic diagram illustrating an example for a relation curve indicating relations between the particle concentration and the moving speed. Please note FIG. 3 is only for example, and does not mean to limit the scope of the present invention. As illustrated in FIG. 3, the portable electronic apparatus 100 in FIG. 1A has a moving speed MS_1 (i.e. the above-mentioned motion data M), which corresponds to a relation curve C_S1. The above-mentioned light sensor 103 acquires the scattered light distribution DSL_1 (i.e. the above-mentioned optical sensed data OS), and the processor 105 in FIG. 1A can map the scattered light distribution DSL_1 to the particle concentration PC_1 based on the relation curve C_S1. For another example, the above-mentioned light sensor 103 acquires the scattered light distribution DSL_2, and the processor 105 in FIG. 1A can map the scattered light distribution DSL_2 to the particle concentration PC_2 based on the relation curve C_S1. Therefore, if the portable electronic apparatus 100 has another moving speed, the relation curve also changes. The optical sensed data OS (ex: DSL_1 & DSL_2) could be a statistic information of the scattered light, such as average intensity received by the light sensor 103 at each time slot (ex: in one captured image or in a predetermined of period) or intensity deviation of each captured image from the light sensor 103.

Accordingly, the processor 105 may acquire another particle concentration even if the scattered light distribution is the same. Please note, the step of calculating the particle concentration based on the motion data M and the scattered light SL_1 is not limited to the example illustrated in FIG. 3. Other methods which can provide the same function should also fall in the scope of the present invention. As above-mentioned, the motion data M can be mapped to a fan speed, therefore, the relation curve can be acquired based on the mapped fan speed rather than the motion data M.

Figure 4:
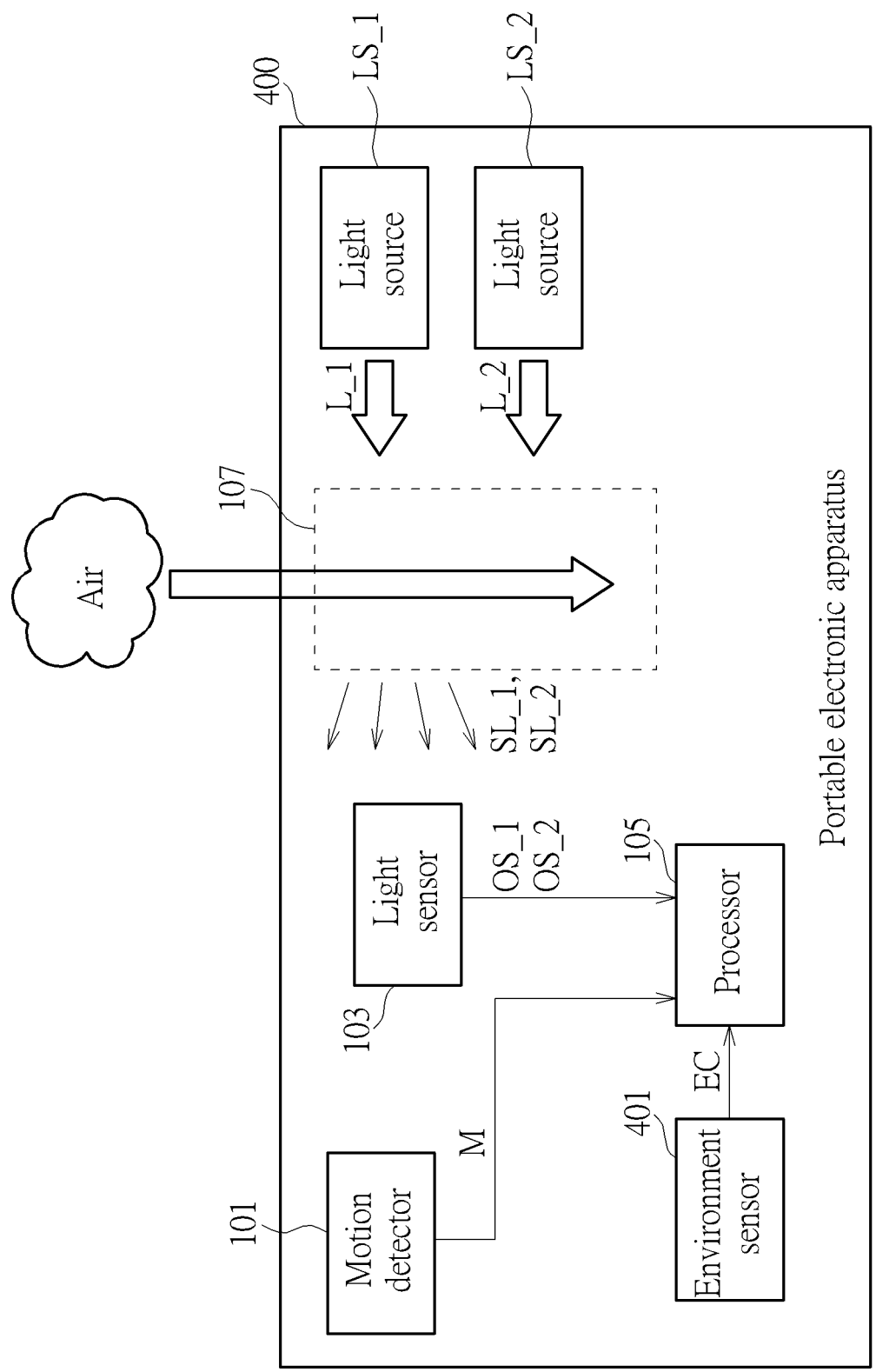
FIG. 4 is a block diagram illustrating a portable electronic apparatus according to another embodiment of the present invention.

In one embodiment, the portable electronic apparatus provided by the present invention can comprise more than one light source. FIG. 4 is a block diagram illustrating a portable electronic apparatus according to another embodiment of the present invention. Comparing the portable electronic apparatus 400 in FIG. 4 with the portable electronic apparatus 100 in FIG. 1A, the portable electronic apparatus 400 further comprises another light source LS_2. The light source LS_2 is configured to emit light L_2. Scattered light SL_2 is generated while the light L_2 emits particles in air. The processor 105 is configured to calculate a particle concentration based on the motion data M and the scattered light SL_1, SL_2 sensed by the light sensor 103. For example, the processor 105 calculates a first particle concentration based on the optical sensed data OS_1 for the scattered light SL_1 and calculates a second particle concentration based on the optical sensed data OS_2 for the scattered light SL_2. After that, the processor 105 calculates a third particle concentration based on the first particle concentration and the second particle concentration.

In one embodiment, the first light source LS_1 and the second light source LS_2 have different spectrums, which may mean different wavelengths. For example, the light source LS_1 emits red light but the light source LS_2 emits blue light. Therefore, the processor 105 may get different particle concentrations even if the motion data and the scattered light distribution for the light sources LS_1, LS_2 are the same.

Please note, although FIG. 4 applies the structure illustrated in FIG. 1A, but the structure in FIG. 1B can be implemented to a portable electronic apparatus having multi light sources as well.

Figure 5:
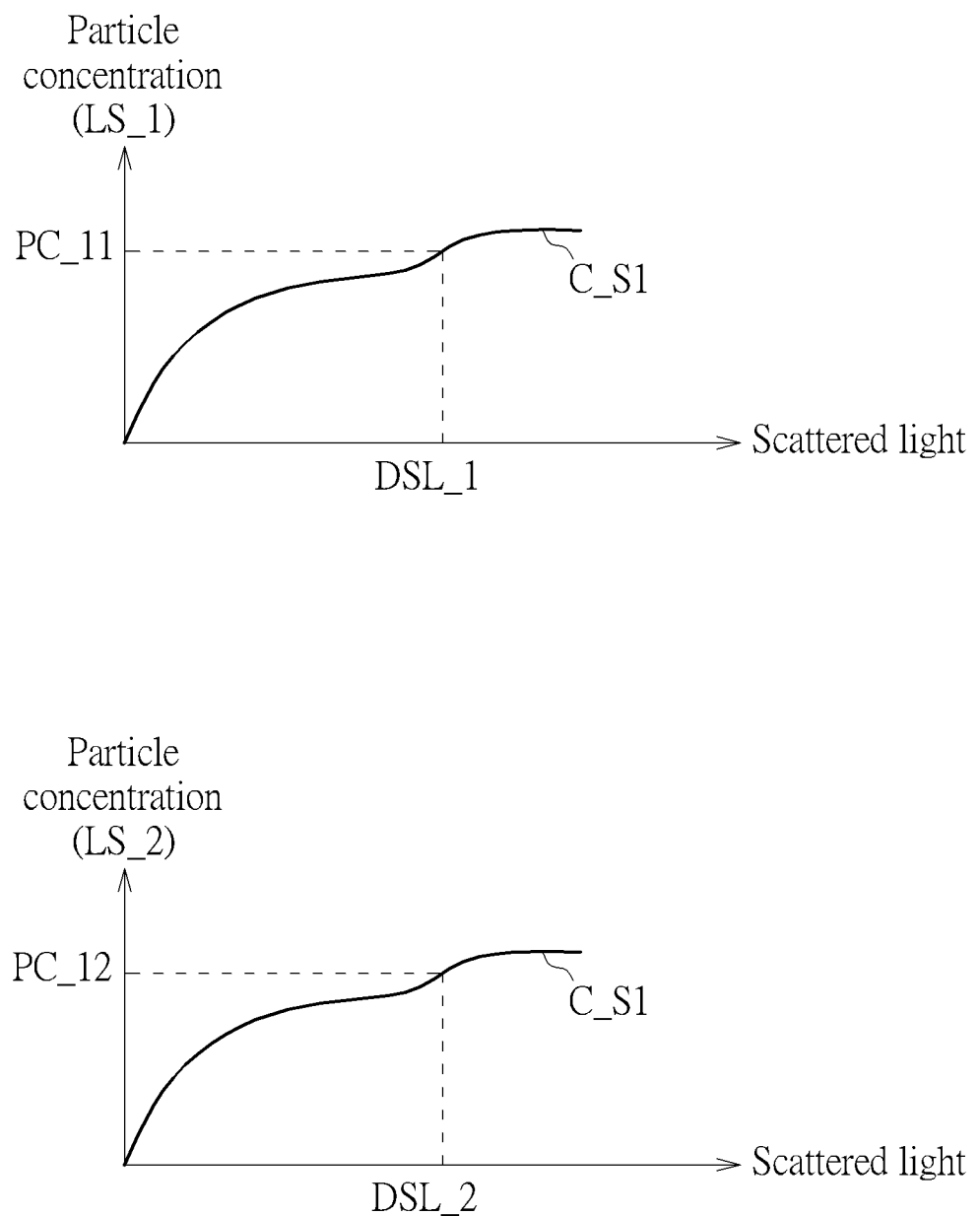
FIG. 5 is a schematic diagram illustrating an example for relation curves indicating relations between the particle concentration and the scattered light, for the embodiment illustrated in FIG. 4.

FIG. 5 is a schematic diagram illustrating an example for relation curves indicating relations between the particle concentration and the scattered light, for the embodiment illustrated in FIG. 4. As illustrated in FIG. 5, the processor 105 will acquire a first particle concentration PC_11 based on the scattered light distribution DSL_1 and the relation curve C_S1, and acquires a second particle concentration PC_12 based on the scattered light distribution DSL_2 and the relation curve C_S1, since different light sources LS_1, LS_2 exist.

In one embodiment, the processor 105 provides a first weighted value W_1 to the first particle concentration PC_11 and provides a second weighted value W_2 to the second particle concentration PC_12, to calculate the third particle concentration PC_13, such as the following Equation (1).

$$(PC\_13)=W\_1\times(PC\_11)+W\_2\times(PC\_12) \quad \text{Equation (1)}$$

In one embodiment, the first weighted value W_1 and the second weighted value W_2 are set to be 0.5, such that the third particle concentration PC_13 comprises average component for each one of the particle concentrations generated based on different light sources. However, the first weighted value W_1 and the second weighted value W_2 can be set to any desired values. Via using more than one light source rather than a single light source, the calculated particle concentration can be more accurate.

In one embodiment, the processor 105 provides the first weighted value W_1 to the first particle concentration PC_11 and provides the second weighted value W_2 to the second particle concentration PC_12 based on an environment condition. For example, the portable electronic apparatus 400 in FIG. 4 further comprises an environment sensor 401, which is configured to sense environment condition such as temperature, moisture, brightness, or any other environment condition. In such case, the processor 105 can determine which one of the light sources is proper for the environment, and increases the corresponding weighted value. For example, if the processor 105 determines red light is more suitable for instant environment, the weighted value corresponding to a light source emitting red light is increased. By this way, the calculated particle concentration can be more accurate since the final particle concentration (ex. the above-mentioned third particle concentration) has more particle concentration calculated based on a proper light source.

In view of above-mentioned embodiments, a particle concentration sensing method can be acquired, which comprises following steps: (a) generating first light (ex. L_1 in FIG. 1A); (b) sensing first scattered light (ex. SL_1 in FIG. 1A), wherein the first scattered light is generated while the first light emitting particles in air; and (c) calculating a first particle concentration based on the motion and the first scattered light sensed by the light sensor. Other detail steps can be acquired based on above-mentioned embodiments, thus are omitted for brevity here.

Figure 6:
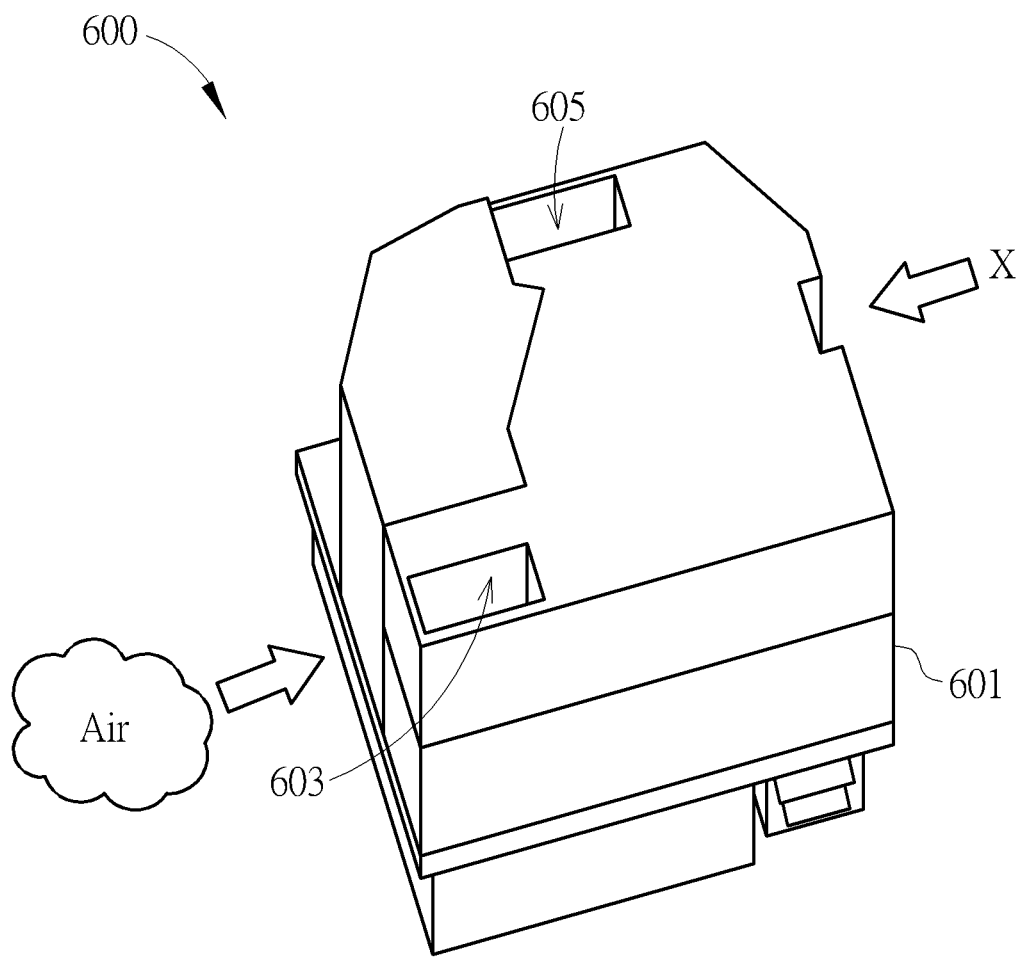
FIG. 6-FIG. 9 are schematic diagrams illustrating examples for mechanical structures of the embodiments illustrated in FIG. 1A and FIG. 4.

FIG. 6-FIG. 9 are schematic diagrams illustrating examples for mechanical structures of the embodiments illustrated in FIG. 1A and FIG. 4. Please note the shape, the size or the location for the components in embodiments illustrated in FIG. 6-FIG. 9 are only for example and do not mean to limit the scope of the present invention. As illustrated in FIG. 6, the portable electronic apparatus 600 comprises a case 601, which comprises an air inlet 603 and an air outlet 605. The air can flow through the air inlet 603 to enter the case 601 and flows through the air outlet 605 to exist the case 601.

Figure 7:
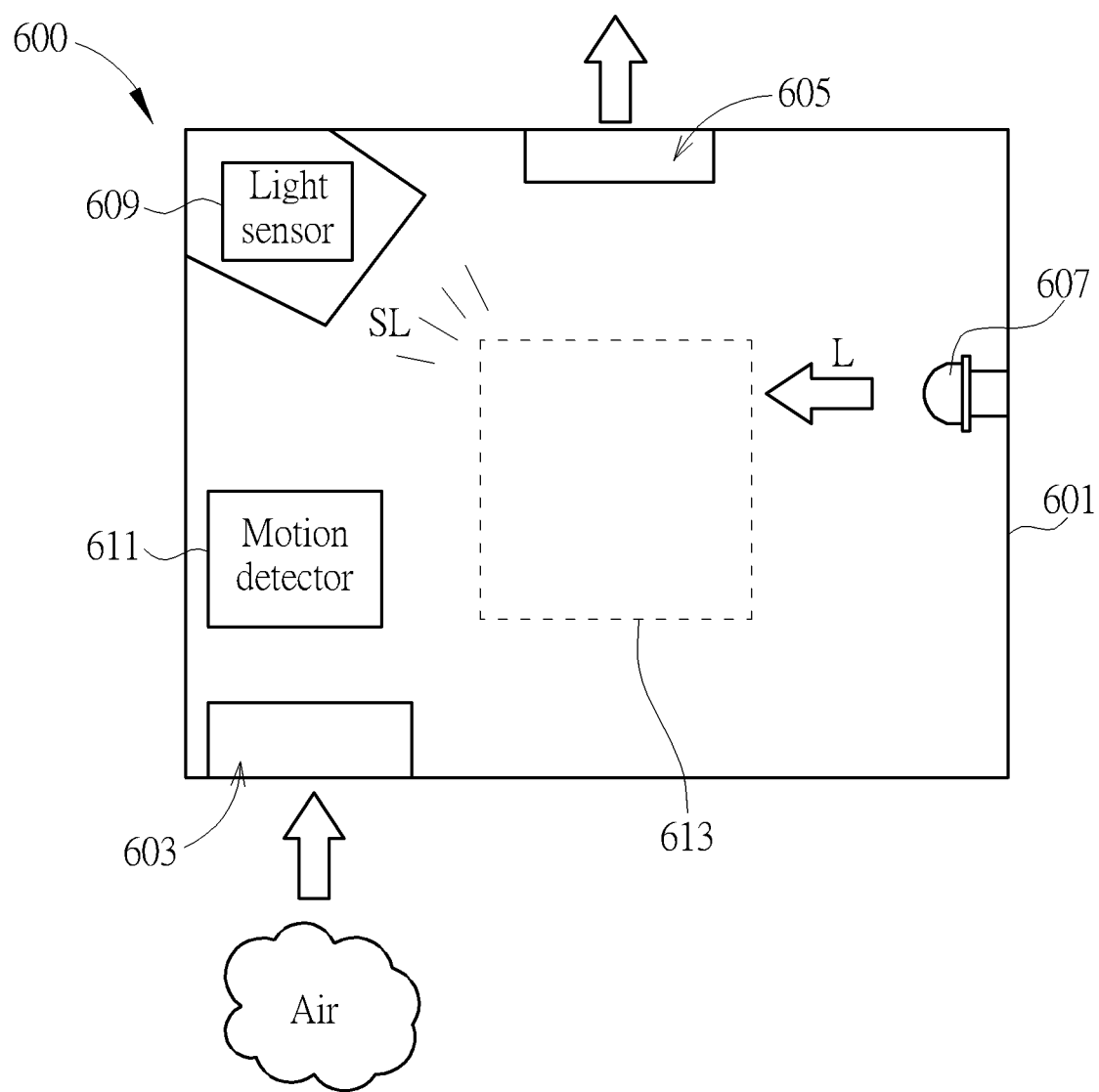

FIG. 7 is a schematic diagram illustrating the internal structure for the portable electronic apparatus 600. As illustrated in FIG. 7, the portable electronic apparatus 600 comprises a light source 607 and a light sensor 609 inside the case 600. As above-mentioned, the light source 607 emits light to the air flowing into the case 601, and scattered light SL is generated while the light L emits particles in the air. Also, the light sensor 609 can sense the scattered light SL. Please note the above-mentioned processor 105 is not illustrated here, but can be provided to any location in the portable electronic apparatus 600. In one embodiment, the case 601 comprises a cavity 613 (ex. the cavity 107 in FIG. 1A and FIG. 1B), and the air can flow into the cavity 613, thereby the light L can emit the air to generate scattered light SL.

Figure 8:
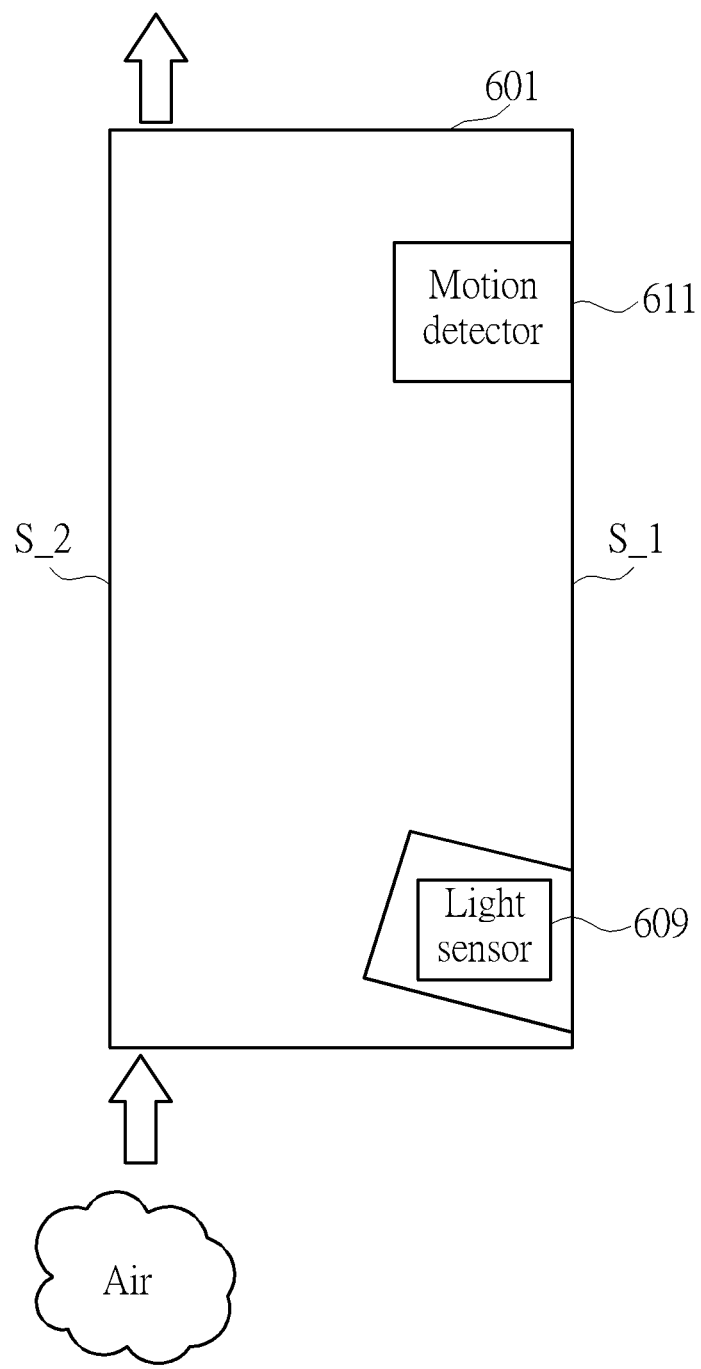
Figure 9:
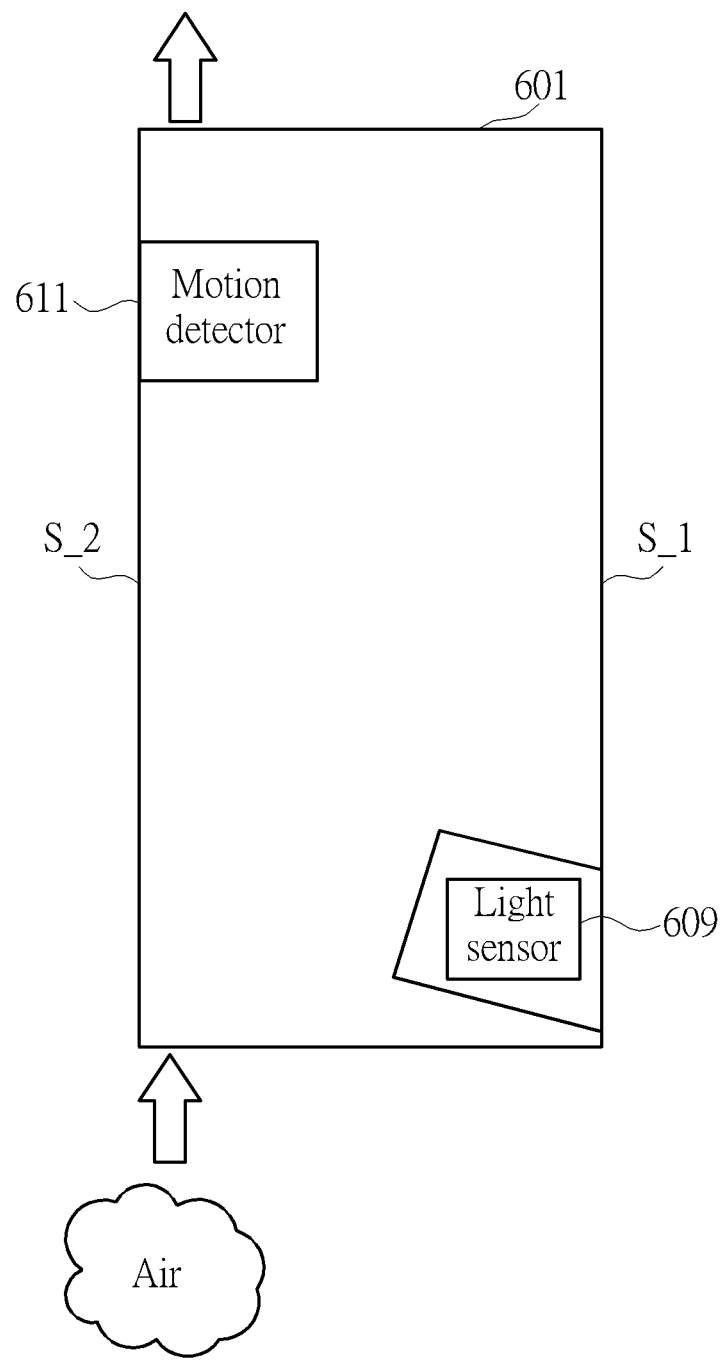

FIG. 8 and FIG. 9 are schematic diagrams illustrated in a view following the X direction in FIG. 6. Please refer to FIG. 8, the case 601 comprises a surface S_1 and a surface S_2. In one embodiment, the light sensor 609 and the motion detector 611 are provided on the same surface. For example, as illustrated in FIG. 8, the light sensor 609 and the motion detector 611 are provided on the surface S_1. In another embodiment, the light sensor 609 and the motion detector 611 are provided on the surface S_2 (not illustrated here).

In another embodiment, the light sensor 609 and the motion detector 611 are respectively provided on different surfaces. As illustrated in FIG. 9, the motion detector 611 is provided on the surface S_2 and the light sensor 609 is provided on the surface S_1. In another embodiment, the motion detector 611 is provided on the surface S_1 and the light sensor 609 is provided on the surface S_2 (not illustrated here). By this way, the light sensor 609 and the motion detector 611 can be provided to suitable locations, for example, corresponding to the shape or the size of the case.

It will be appreciated that the embodiments in FIG. 8 and FIG. 9 are only for example, the light sensor and the motion detector can be provide on any other surface(s) of the case 601.

Figure 10:
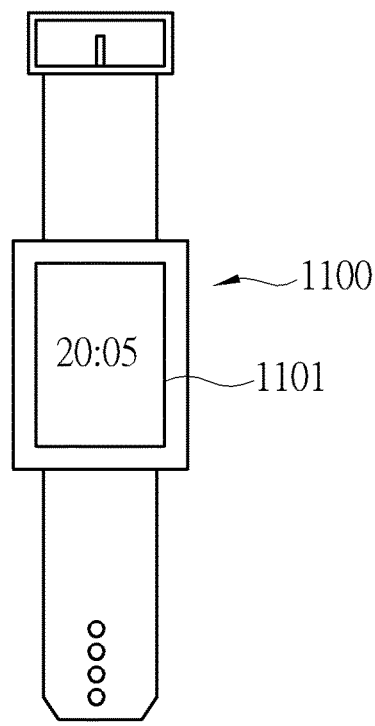
FIG. 10-FIG. 11 are schematic diagrams illustrating an example of practical application for the portable electronic apparatus provided by the present invention.
Figure 11:
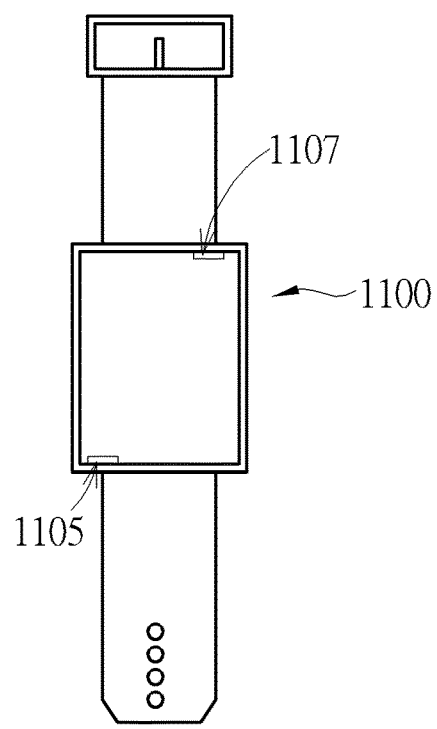

As above-mentioned, the portable electronic apparatus can be a wearable electronic apparatus, such as a smart watch or a smart bracelet. FIG. 10 and FIG. 11 illustrate the above-mentioned particle concentration sensing method is applied to a watch. FIG. 10 illustrates a front of the watch 1100, which may comprise a display 1101 to show time or any other information. FIG. 11 illustrates a back of the watch 1100, which may comprise an above-mentioned air inlet 1105 and an above-mentioned air outlet 1107. If a user wears the watch 1100 and waves his hand or walks, the air can flow into the watch 1100 via the air inlet 1105, and the particle concentration can be calculated based on above-mentioned embodiments.

Please note, the above-mentioned particle concentration sensing method can be applied to any other portable electronic apparatus besides the above-mentioned wearable apparatus, such as a smart phone or a tablet computer. In one embodiment, the size of the portable electronic apparatus is too small and could not allow a fan to be provided in the portable electronic apparatus, thus use the particle concentration sensing method provided by the present invention.

In view of above-mentioned embodiments, the particle concentration can be calculated without a fan, and the accuracy for calculating particle concentration can be increased if more than one light source is employed. Further, applying a CMOS light sensor can decrease the size of the light sensor.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A portable electronic apparatus can sense particle concentration, comprising:
   a motion detector, configured to detect a motion of the portable electronic apparatus;
   a first light source, configured to emit first light, wherein first scattered light is generated while the first light emitting particles in air flowing into the portable electronic apparatus;
   a second light source, configured to emit second light;
   a light sensor, configured to sense the first scattered light; and
   a processor, configured to calculate a first particle concentration based on the motion and the first scattered light sensed by the light sensor;
   wherein second scattered light is generated while the second light emitting particles in the air;
   wherein a spectrum of the first light and a spectrum of the second light are different;
   wherein the processor calculates a second particle concentration based on the motion and the second scattered light sensed by the light sensor, and calculates a third particle concentration based on the first particle concentration and the second particle concentration.

2. The portable electronic apparatus of claim 1, wherein the portable electronic apparatus is a wearable electronic apparatus.

3. The portable electronic apparatus of claim 1, wherein the motion detector is an accelerometer or a gyroscope.

4. The portable electronic apparatus of claim 1, wherein the processor provides a first weighted value to the first particle concentration and provides a second weighted value to the second particle concentration, to calculate the third particle concentration.

5. The portable electronic apparatus of claim 4, wherein the processor provides the first weighted value to the first particle concentration and provides the second weighted value to the second particle concentration based on an environment condition.

6. The portable electronic apparatus of claim 1, wherein the light sensor is a CMOS light sensor.

7. The portable electronic apparatus of claim 1, wherein the processor maps the motion to a fan speed, and calculates the first particle concentration based on the fan speed and the first scattered light sensed by the light sensor.

8. The portable electronic apparatus of claim 1, wherein a size of the portable electronic apparatus could not allow a fan to be provided in the portable electronic apparatus.

9. The portable electronic apparatus of claim 1, further comprising a first surface inside the portable electronic apparatus, wherein the motion detector and the light sensor are provided on the first surface.

10. The portable electronic apparatus of claim 1, further comprising a first surface inside the portable electronic apparatus and a second surface opposite to the first surface, wherein the motion detector is provided on the first surface and the light sensor is provided on the second surface.

11. A particle concentration sensing method, applied to a portable electronic apparatus, comprising:
   (a) generating first light;
   (b) sensing first scattered light, wherein the first scattered light is generated while the first light emitting particles in air flowing into the portable electronic apparatus; and
   (c) calculating a first particle concentration based on the motion and the first scattered light sensed by the light sensor;
   wherein the particle concentration sensing method further comprises:
   generating second light, wherein a spectrum of the first light and a spectrum of the second light are different;
   calculating a second particle concentration based on the motion and second scattered light sensed by the light sensor, and calculates a third particle concentration based on the first particle concentration and the second particle concentration;
   wherein second scattered light is generated while the second light emitting particles in the air.

12. The portable electronic method of claim 11, wherein the portable electronic apparatus is a wearable electronic apparatus.

13. The portable electronic method of claim 11, wherein the motion detector is an accelerometer or a gyroscope.

14. The portable electronic method of claim 11, further comprising:
   providing a first weighted value to the first particle concentration and providing a second weighted value to the second particle concentration, to calculate the third particle concentration.

15. The portable electronic method of claim 14, further comprising:
   providing the first weighted value to the first particle concentration and provides the second weighted value to the second particle concentration based on an environmental condition.

16. The portable electronic method of claim 11, wherein the light sensor is a CMOS light sensor.

17. The portable electronic method of claim 11, wherein the step (c) maps the motion to a fan speed, and calculates the first particle concentration based on the fan speed and the first scattered light sensed by the light sensor.

18. The portable electronic method of claim 11, wherein a size of the portable electronic apparatus could not allow a fan to be provided in the portable electronic apparatus.

* * * * *